(12) United States Patent
Sorensen

(10) Patent No.: US 6,794,495 B1
(45) Date of Patent: Sep. 21, 2004

(54) COMPOSITION COMPRISING EXTENSIN AND, OPTIONALLY, PECTIC POLYSACCHARIDES

(75) Inventor: Marinus Blaabjerg Sorensen, Hvalso (DK)

(73) Assignee: New Nordic Danmark APS, Roskilde (DK)

(*) Notice: Subject to any disclaimer, the term of this patent is extended or adjusted under 35 U.S.C. 154(b) by 0 days.

(21) Appl. No.: 09/419,927

(22) Filed: Oct. 18, 1999

Related U.S. Application Data

(60) Provisional application No. 60/104,720, filed on Oct. 19, 1998.

(51) Int. Cl.[7] ............................ C07K 1/00; C08B 37/06; A01N 43/04
(52) U.S. Cl. ............................... 530/395; 536/2; 514/54
(58) Field of Search ............................ 530/395; 536/2; 514/54

(56) References Cited

PUBLICATIONS

Li et al., "A chenopod extensin lacks repetetive tetra hydroxyproline blocks", Plant Physiology, vol. 92, issue 2, pp. 327–333, 1990.*

Qi et al. Solublization and Partial Characterization of Extensin, Plant Physiology, vol. 108, No. 4, pp. 1691–16701, Aug. 1995.*

Pienta et al., Inhibition of Spontaneous Metastasis in a Rat Prostate Cancer Model by oral Administration of Modified Citrus Pectin, Journal of the National Cancer Institute, vol. 87, No. 5, Mar. 1, 1995.

* cited by examiner

*Primary Examiner*—Gary Kunz
*Assistant Examiner*—Fozia Hamud
(74) *Attorney, Agent, or Firm*—Levy & Grandinetti

(57) ABSTRACT

The invention is a compound and method for enhancing the immune system. The compound is extensin or a combination of (a) pectin or polysaccharides found in the pectic molecule and (b) extensin. The method for cytotoxic enhancement of lymphocytes requires ingesting a therapeutically effective amount of extensin or a combination of pectin or polysaccharides found in the pectic molecule and extensin to enhance the activity of the immune system. The invention also relates to a method for preparing a therapeutically effective pharmaceutical for the cytotoxic enhancement of lymphocytes.

5 Claims, No Drawings

COMPOSITION COMPRISING EXTENSIN AND, OPTIONALLY, PECTIC POLYSACCHARIDES

I claim the benefit under Title 35, United States Code 120 U.S. Provisional Application No. 60/104,720, filed Oct. 19, 1998, entitled PROTEIN EXTENISON AND METHOD FOR CYTOTOXIC ENHANCEMENT OF LYMPHOCYTES.

BACKGROUND OF THE INVENTION

1. Field of the Invention

The invention relates to a compound which, through biological signals towards lymphocytes, induces development and maturation of lymphocytes and method to control the cytotoxic enhancement of lymphocytes in the intestine. The invention can be used as a therapeutic method to modulate immune responses in the prevention and treatment of a broad variety of disorders including infections and cancers.

2. Description of the Related Art

Epidemiological studies have provided evidence that dietary components in food influence the development of illnesses, e.g., infections and cancers, in human populations. The immune system combines several different strategies in dealing with abnormal cells (cancer) or foreign organisms (viruses, bacteria, parasites). Exposure of blood cells to foreign or abnormal molecules (antigens) stimulates the growth of specialized white cells (B lymphocytes) which produce antibodies. These circulate in the blood or concentrate at mucosal surfaces such as the lungs, the nose, and the intestines, which are prime entry points for invading organisms. The antibodies recognize and bind with high specificity to their target, marking it out for disposal by the scavenger cells of the body. Even in the absence of a specific immune response, these scavenger cells play an important role in body defenses. Phagocytes and natural killer cells recognize and destroy cancer cells, viruses, and parasites as well as stimulate other components of the immune system. An important aspect of long-term immunity is stimulation of other white cells (T lymphocytes) by antigens. The T cells produce cytokines which increase the effectiveness of scavenger cells. At the same time, the scavenger cells take up antigens and display fragments of these foreign proteins of their surfaces, increasing T cell stimulation.

The intestinal mucosal immune system is adapted to protect the host against potential pathogens. Thus, a complex population of T lymphocytes can be found in the gut-associated lymphoid tissues (GALTs). Lymphocytes are localized in the Peyer's patches, the lymphoid follicles in the colonic mucosa, in the intestinal lamina propria, and above the basement membrane between epithelial cells, i.e., they are lamina propria lymphocytes (LPLs) and intraepithelial lymphocytes (IELs). More than 95 percent of human LPLs have the alpha/beta isotype of the antigen-specific T-cell receptor (TCR). Additionally, CD4- and CD8-positive T cells are present in the laminapropria and in the peripheral blood in a similar proportion. Usually, immature precursors of T lymphocytes from haematopoietic sources are matured in the thymus, i.e., genes that encode the alpha- and beta-chains of their receptors are rearranged. However, extrathymic T cells which differentiate in the intestines or the liver seems to stand at an intermediate position between natural killer (NK) cells and thymus-derived T cells in the phylogenetic development. The ability of the intestine to induce development and maturation of extrathymic T cells, e.g., LPLs and IELS, makes phylogenetic sense. From an evolutionary point of view, GLATs constitute the first distinct lymphoid tissues in vertebrates, appearing prior to the spleen, the thymus, the bone marrow, and the lymph nodes.

Extrathymic T cells play a role in (a) aging, (2) conditions of malignancy at tumor sites, (3) intracellular infections, (4) pregnancy, (5) autoimmune diseases, and (6) elimination of abnormal self-cells generated by the body itself. Pathways of T cells may increase, accompanying acute thymic atrophy. Intestinal epithelium may induce IEL development without the action of thymic-derived products, or a thymus may promote extrathymic development processes either directly or indirectly. Recent findings give empirical evidence that alternative mechanisms exist for rendering IELs tolerant of normal host tissues. Thus the intestinal epithelium has an intricate and well-refined process for the elimination of autoreactive T cells in a thymus-independent manner.

Pectins are soluble dietary fibers, which are completely metabolized in the gut due to bacterial fermentation. Pectin is a complex mixture of colloidal polysaccharides found in the primary cell walls of dicotyledons (dicots). In vitro test has demonstrated that several polysaccharides contained in pectin have immune stimulating actions. Rhamnogalacturonan enhance the cytotoxic activity of human natural killer (NK) cells and T cells, arabinogalactan activate macrophage and reduce or inhibit metastasis.

In 1994, an in vivo experiment was designed in Michigan by Avraham Raz, Kenneth Pienta, and coworkers. Laboratory animals were fed with citrus pectins in the drinking water. The purpose was to see if pectic polysaccharides influenced primary tumor growth and metastasis. Male Copenhagen rats had fast-growing, prostate adenocarcinoma cells injected into their thigh. This resulted in death of control animals within approximately 25 days. However, if the primary tumor was removed before metastasis after about 10 days, control animals could be saved from dying. Interestingly, rats consuming 1.0 percent w/v citrus pectins per day from day four showed a significant reduction in spontaneous lung metastases. Additionally, a significant reduction in the average frequency of metastases per lung was observed. This work was reported in an article by Pienta et al., "Inhibition of Spontaneous Metastasis in a Rat Prostate Cancer Model by Oral Administration of Modified Citrus Pectin," Journal of the National Cancer Institute, Vol. 87, No. 5, Mar. 1, 1995.

SUMMARY OF THE INVENTION

The compound comprises the protein extensin or a combination of (1) pectin or polysaccharides found in the pectic molecule and (2) extensin.

The invention relates to a method for using extensin or a combination of pectin or polysaccharides found in the pectic molecule and extensin which is beneficial to health because it can enhance the activity of the immune system.

The invention also relates to a method for preparing a therapeutically effective pharmaceutical for the cytotoxic enhancement of lymphocytes.

DESCRIPTION OF THE INVENTION

Pectin is a complex mixture of colloidal polysaccharides found in the primary cell walls of dicotyledons (dicots). It is characterized by the presence of rhamnose (L-Rhap), galacturonic acid (D-GalpA), arabinose (L-Araf), and galactose (D-Galp). Traditionally, pectin is known for the gellifying properties utilized in industrial and household preparations of jellies, jam, and marmalade. Novel use of pectin includes pharmaceuticals, e.g., barrier antacids, protective barrier between tape and skin, and wound dressings in which the hydrophilic polymer creates a moist environment that is advantageous for a more rapid recovery process. Fibers, e.g., pectins, have a positive role in the human diet. Pectin has a backbone of -1,4-D-galacturonan alternating with rhamnogalacturonan-1 (RG-1). -1,4-D-Galacturonan is composed of about one hundred consecutive -(1 4)-linked D-GalpA residues, and the RG-1 backbone which contains D-GalpA and L-Rhap residues has a degree of polymerization up to about 20. Side chains of arabinan, arabinogalactan, and/or galactan are mostly substituted on O-4 of L-Rhap residues and characteristic glycosidic linkages in side chains have been determined. Three-dimensional computer analysis of the pectic backbone has revealed that it is nearly a linear structure. Side chains, e.g., arabinogalactan-II (AG-II), are connect d at almost a right angle to the backbone of RG-1 resulting in a parsley mill structure. These side chains presumably form a hydrophilic network that can retain water within the matrix of cell walls. It is also possible that neighboring backbones have interlacing side chains that make a strong architecture with many weak hydrogen bonds.

Pectins are a mixture of polysaccharides that have a varying degree of neutralization. Pectinic acids and pectinates contain some ester groups whereas pectic acids or pectates have a negligible amount of ester groups. Esterified D-GalpA prevents an enzymatic cleavage of -1,4-D-galacturonan by fungal endo-polygalacturonase (E.C.3.2.1.15). This poly-1 4- -D-galacturonide glycanohydrolase (endo-PG) catalyzes the hydrolysis of -1,4-bonds in demethylated and deacetylated D-galacturonan. It has been shown that oligosaccharide fragments of D-galacturonan are elicitors that induce plant tissue to synthesize phytoalexins which are toxic compounds to fungi. The complex polysaccharide that is left after an endo-PG digestion is RG-1 which has a major glycosyl composition of L-Rhap, D-GalpA, L-Araf, and D-Galp residues. Polysaccharides can be converted into their monosaccharide constituents using hydrolysis at 121° C. for one hour with 2 M trifluoroacetic acid. The loss of sugars is moderate, and derivatization is not needed if the monosugars are separated on a CarboPac PA1 column (Dionex Corp.) and measured by pulsed amperometric detection. Rhamnogalacturonan-1 has been solubilized from suspension-cultured sycamore cell walls (*Acer pseudoplatanus*), and a molecular weight of approximately 200 kDa has been estimated.

Arabinans are branched polysaccharides composed of -1,5-linked chains of L-Araf residues substituted at O-3, and galactans are -(1 4)-linked polymers of D-Galp residues with some 6-linked D-substituted at O-3, and galactans are -( 4)-linked polymers of D-Galp residues with some 6-linked D-Galp residues. Arabinogalactans are grouped into two types. The AG-1 is a -1,4-linked D-Galp backbone substituted through O-3 with side chains of D-Galp residues. This is found in pectins-in seeds, bulbs, and leaves. Apparently, AG-II is more widespread in gymnosperms and angiosperms, in seeds, leaves, roots, fruits, gums, saps, and exudates. It is a very branched polymer that contains a backbone of (1 3)- -linked D-Galp residues with side chains of (1 6)- -linked D-galactooligosaccharides that may have L-Araf residues linked (1 3) or (1 6) to the D-Galp residues. Arabinose residues may be attached to each other by (1 3) and/or (1 5)-links. Plant gums are commercially valuable, and the intensively studied gums from acacia (*Acacia senegal*) and related species are usually water-soluble polymers. In health care, small arabinogalactans may be candidates for hepatocyte-directed drug delivery.

Extensin is a hydroxyproline-rich glycoprotein (HRGP) particularly abundant in the cell walls of dicots. Extensin contains the amino acids: valine, tyrosine, histidine, threonine, and lysine. Extensin is a rodlike molecule characterized by a polyproline-II helical structure which stabilizes molecular shape and makes hydrogen bond formations possible to adjacent molecules. In the carrot, Araf and Galp residues comprise 65 percent of the weight of an 86 kDa extensin, 97 and 3 percent, respectively. Hydroxyproline residues comprise 45 percent of the protein, and the proportion of polyprolin -II conformation can be determined from circular dichroism studies. Deglycosylation by hydrogen fluoride caused much of the helical secondary structure to be lost. This indicates that the carbohydrates are essential for the native conformation of the protein backbone.

Extensin is synthesized as a soluble monomer and subsequently polymerized into an insoluble polymer in the cell wall. The Golgi apparatus is the site of assembly of glycoproteins. The protein moiety of extensin is about one-third of the total weight, and abundant amino acids are trans-4-L-hydroxyproline to which are attached short carbohydrate side chains: serine, valine, tyrosine, histidine, threonine, and lysine. Repeating motifs are commonly recognized, e.g., Ser-Hyp4 and Val-Tyr-Lys, and similarities exist between different plant species. However, the tetra-hydroxyproline block has not been found in the sugar beet in which the sequence is interrupted: Ser-Hyp2-S- Hyp2-Thr-Hyp-Val-Tyr-Lys. Here X represents an insertion of Val-His-Glu Lys-Tyr-Pro. Apart from this, the sugar beet extensin has a repeating sequence of amino acids analogous to the sequences found in tomato (*Lycopersicon esculentum*), carrot (*Daucus carota* L.), and tobacco (*Nicotiana tabacum*). The hydroxylation of proline residues is a post-translational modification by prolyl hydroxylases (E.C. 1.14.11.2), that may depend on the amino acid sequence in the extensin molecules. Thus, the dipeptide sequences Lys-Pro, Tyr-Pro, and Phe-Pro are not found to be hydroxylated in contrast to Pro-Val. Complete sequences of extensins are not easily determined because they are usually insoluble. One approach is to investigate the soluble precursors of extensin, or to screen for extensin in a cDNA library. In dicots, hydroxyproline residues may be O-glycosylated with a single sugar (arabinose or galactose) or up to four Araf residues in an arabino-oligosaccharide. Most of the serine residues, e.g., the Ser-Hyp4 repeats in particular, are O-glycosylated with a single Galp residue. Prolyl hydroxylase appears to be an important enzyme for normal cell morphology. Tobacco protoplasts treated with micromolar concentrations of 3,4-dehydro-L-proline, which is a selective inhibitor of prolyl hydroxylase, developed an abnormal cell wall structure, and cell division was inhibited.

The plant cell wall proteins are divided into five classes. Although differences exist, common features have been identified. Like extensin, the proline-rich proteins (PRPs) are insolubilized in the cell wall, and the relatively high content of tyrosine residues in PRPs can participate in isodityrosine cross-links. The potato tuber lectin (a solanaceous lectin) has a serine-hydroxyproline-rich glycopeptide domain that resembles extensin, and this can also accumulate in response to wounding. Solanaceous lectins are apparently associated with cell membranes instead of cell walls, and they are glycosylated the same way as extensin. Glycine-rich proteins (GRPs) may contain up to 70 percent glycine residues arranged in short repeats, and GRPs are like extensin expressed in response to a variety of developmental and stress conditions.

Tissue-specific expression of xtensin has been examined by immunolocalization in the light microscope in leaves, stems, roots, fruit, and tuber of carrot, tomato, and potato, and all cells displayed a varying degree of staining. The functions of extensin have focused attention to developmental control, defense against various pathogens, e.g., fungi, bacteria, and viruses, and wound healing. Wounding induces a rapid activation of a specific class of serine threonine protein kinases, and this suggests the presence of an intracellular signal transduction pathway related to the wound stimulus. Moreover, extensin may link covalently to other cell wall macromolecules, e.g. arabinogalactan and rhamnogalacturonan-1 (RG-1). Evidence for a covalent cross-link between extensin and RG-1 has come from the studies of cell walls from cotton (*Gossypium hirsutum* L.). Cell walls of suspension cultures were subjected to endo-polygalacturonase, cellulose (endo- -1,4-D-glucanase, E.C. 3.2.1.4), anhydrous hydrogen fluoride solvolysis, ammonium bicarbonate extraction, and trypsin (E.C. 3.4.21.4). After this treatment, only sugars indicative of RG-1 and extensin remained in soluble.

Following in vitro testing of polysaccharides found in pectin, we have done scientific in vitro experiments to test synergistic effects of pectic molecules and extensin. We identified that a combination of pectic molecules with the protein extensin containing valine, tyrosine, histidine, threonine, and lysine can activate eukaryotic cells in significantly smaller concentrations than pectic molecules alone. A combination of pectin with extensin in a ratio higher than seen in natural plant cells can be used as a therapeutic method to modulate immune responses in the treatment of a broad variety of disorders including infections and cancers.

In summary, the present invention relates to the protein extensin, a combination of compounds which comprise (1) extensin, or (2) a combination of pectin or polysaccharides found in the pectic molecule and extensin, being able to induce development and maturation of extrathymic lymphocytes.

The invention can be used as a method to enhance the cytotoxic activity of lymphocytes in relation to conditions of malignancy at tumor sites, intracellular infections, autoimmune diseases, and elimination of abnormal self-cells generated by the body itself.

The invention was the result of a laboratory test program using in vivo cell signalling model. The application of a nutritionally complete synthetic (NCS) medium in an oligo-cell experimental research program in which cells demise (or eventually have a prolonged lag-phase) was used for gaining scientific information related to determining the effectiveness of pectins and pectin and extensin combinations as biochemical messengers. An additional control was supplemented with cephalin, that activates cells to multiplication. The effect of an activator added to the NCS medium is compared directly to the control that demises. Apparently, any compound or combination of compounds can be examined in light of the question whether it can activate a cell to survive and/or proliferate. From the beginning of the 1980's the effect of biochemical messengers has been examined with cells grown in an NCS medium free of proteins, lipids, and sugars. Signalling applies to unicellular and multicellular organisms, and the idea of NCS media is that a biochemical messenger can be tested for its biological effect on the cells to gain insight in cellular signalling mechanisms.

Biochemical messengers are related to the four biological cornerstones of the eukaryotic cell: survival, proliferation, differentiation, and programmed cell death.

In oligo-cell experiments, different pectins and combinations of pectins and extensins were examined for their ability to activate *Tetrahymena thermophila* cells to survival and/or proliferation. The Tetrahymena cell has nutritional requirements similar to those of animals. They contain subcellular organelles such as mitochondria and peroxisomes, which are essential for the development of regulatory mechanisms in cellular metabolism. Although, apparent differences in phylogenesis exist between unicellular species and multicellular species, it is of interest that they have similarities, which justify the use of Tetrahymnea as a substitute for mammal cells in this investigation, e.g., biochemical messengers, signal transduction pathways, or resemblance of structural components. Two examples are the *T. thermophila* ribosomal protein S/ which is homologous to mammalian ribosomal protein S4, and the carbohydrate metabolism which is closely related to that of mammals. Glycogenesis, glycolysis, tricarboxylic acid cycle, and lipid metabolism have been reviewed. Cloning efficiencies were evaluated after 30 hours and compared to the controls that were supplemented with c phalin which showed cloning efficiencies of 92 percent. When a combination of pectins and extensin was added *T. thermophila* cells were activated, and the best survival frequency was demonstrated. None of the other compounds test d activated *T. thermophila*.

EXAMPLE

Pectin Containing Extensin

This experiment was set up to evaluate the effectiveness of different types of pectins with different content of proteins (extensin) and a partially purified extensin.

| Oligo-cell experiments with Tetrahymena thermophilia | | |
|---|---|---|
| Composition of medium | mg/L | Cloning efficiencies |
| Synthetic nutrient medium |  | 0/15 |
| cephalin | 50 | 15/15 |
| extensin partially purified from sugar beet pectin | 25 | 12/15 |
| citrus pectin | 25 | 3/15 |
| citrus pectin saponificated | 25 | 3/15 |
| beet pectin | 25 | 8/15 |
| beet pectin saponificated | 25 | 1/15 |
| apple pectin | 25 | 4/15 |
| apple pectin saponificated | 25 | 1/15 |

The initial cell concentration was about two cells in a two-mL volume.

Cloning efficiencies were determined from cell multiplications in a synthetic nutrient medium without and with supplements. The first number given was the number of experiments that had multiplication of cells after 30 hours. The second number given was the total number of experiments.

In,the above experiment the partially purified xtensin showed cloning efficiencies of 80 percent. The extensin was partially purified from sugar beet pectin (*Beta vulgaris*). The partly purified extensin can be described as rhamnogalacturonan proteins containing non-covalent bonds between hydroxyproline-rich glycoproteins and rhamnogalacturonan-1.

Native nonsaponificated pectin is apparently more effective than saponified pectin. The data suggest that pectins with a higher protein (and extensin) content are more effective than pectins with lower protein content.

As the purified extensin is difficult and expensive to commercialize in larger scale, this experiment aimed to see if similar effects could be obtained by protein (extensin) rich fibers from sugar beet alone or if there would be a synergistic advantage of combining pectin with protein/extensive rich fibers from sugar beet.

| Oligo-cell experiments with tetrahymena thermophilia | | |
|---|---|---|
| Composition of medium | mg/L | Cloning efficiencies |
| Synthetic nutrient medium | | 0/15 |
| cephalin | 50 | 15/15 |
| extensin partially purified from sugar beet pectin | 25 | 11/15 |
| sugar beet fiber | 25 | 11/15 |
| 50% citrus pectin/ 50% sugar beet fiber | 25 | 3/15 |
| 50% beet pectin/ 50% sugar beet fiber | 25 | 15/15 |
| 50% apple pectin/ 50% sugar beet fiber | 25 | 10/15 |

The initial cell concentration was about two cells in a two-mL volume.

Cloning efficiencies were determined from cell multiplications in a synthetic nutrient medium without and with supplements. The first number given was the number of experiments that had multiplication of cells after 30 hours. The second number given was the total number of experiments.

What is claimed is:

1. A composition comprising:

A) 50% of an extensin; and

B) 50% of at least one pectin;

wherein:

said extensin comprises at least one sequence selected from the group consisting of A) Ser-Hyp2-Val-His-Glu-Tyr-Pro-Hyp2-Thr-Hyp-Val-Tyr-Lys, and B) Ser-Hyp2-Val-His-Lys-Tyr-Pro-Hyp2-Thr-Hyp-Val-Tyr-Lys;

and is free from the sequence Ser-Hyp-Hyp-Hyp-Hyp.

2. The composition of claim 1 wherein the pectin is sugar beet pectin.

3. The composition of claim 1 wherein the pectin is citrus pectin.

4. The composition of claim 1 wherein the pectin is apple pectin.

5. The composition of claim 1 wherein the extensin is provided by sugar beet fiber.

* * * * *